(12) United States Patent
Mossanen-Shams

(10) Patent No.: US 7,658,717 B2
(45) Date of Patent: Feb. 9, 2010

(54) PULMONARY EVALUATION DEVICE

(76) Inventor: Iden Mossanen-Shams, 35 Norton Road, Uxbridge, UB8 2PT (GB)

( * ) Notice: Subject to any disclaimer, the term of this patent is extended or adjusted under 35 U.S.C. 154(b) by 10 days.

(21) Appl. No.: 10/567,871

(22) PCT Filed: Aug. 10, 2004

(86) PCT No.: PCT/GB2004/003472

§ 371 (c)(1),
(2), (4) Date: Feb. 9, 2006

(87) PCT Pub. No.: WO2005/016145

PCT Pub. Date: Feb. 24, 2005

(65) Prior Publication Data

US 2006/0276717 A1    Dec. 7, 2006

(30) Foreign Application Priority Data

Aug. 13, 2003    (GB) .................. 0318935.4

(51) Int. Cl.
A61B 5/08 (2006.01)
A61B 5/103 (2006.01)
A61B 5/117 (2006.01)

(52) U.S. Cl. .................. 600/534; 600/538; 600/595

(58) Field of Classification Search ......... 600/529–543, 600/493, 459, 483, 301, 388–390, 382, 384, 600/393, 300, 595, 481, 484
See application file for complete search history.

(56) References Cited

U.S. PATENT DOCUMENTS

| | | | | |
|---|---|---|---|---|
| 4,183,247 A | * | 1/1980 | Allen et al. | 73/863.02 |
| 4,187,859 A | * | 2/1980 | Allen et al. | 600/538 |
| 4,245,651 A | * | 1/1981 | Frost | 600/534 |
| 4,308,872 A | * | 1/1982 | Watson et al. | 600/538 |
| 4,324,259 A | | 4/1982 | Wright | |
| 4,559,953 A | | 12/1985 | Wright et al. | |
| 4,572,197 A | * | 2/1986 | Moore et al. | 600/389 |
| 4,730,625 A | * | 3/1988 | Fraser et al. | 600/594 |
| 4,807,640 A | * | 2/1989 | Watson et al. | 600/534 |
| 4,884,578 A | * | 12/1989 | Morgenstern | 600/483 |
| 4,920,969 A | * | 5/1990 | Suzuki et al. | 600/436 |
| 4,928,674 A | * | 5/1990 | Halperin et al. | 601/44 |
| 5,007,427 A | * | 4/1991 | Suzuki et al. | 600/436 |
| 5,020,516 A | * | 6/1991 | Biondi et al. | 601/44 |
| 5,022,402 A | * | 6/1991 | Schieberl et al. | 600/484 |
| 5,111,818 A | * | 5/1992 | Suzuki et al. | 600/390 |
| 5,159,935 A | * | 11/1992 | Sackner et al. | 600/534 |

(Continued)

FOREIGN PATENT DOCUMENTS

DE    199 37 836 A1    2/2001

(Continued)

Primary Examiner—Charles A Marmor, II
Assistant Examiner—Navin Natnithithadha
(74) Attorney, Agent, or Firm—Workman Nydegger

(57) ABSTRACT

Pulmonary evaluation device has sensor means adapted to sense fluctuations in a user's lung operation and feedback means, driven by said sensor means, for determining successive values representative of the user's lung fluctuations and adapted to translate said values into appropriate lung-evaluating information. Optionally, the sensor means comprises or forms part of an item suitable to be worn by or carried adjacent the user so as to follow body movements caused by the user's lung operation to evaluate the user's lung operation.

14 Claims, 3 Drawing Sheets

U.S. PATENT DOCUMENTS

| | | | | |
|---|---|---|---|---|
| 5,191,893 | A | * | 3/1993 | Reiten .................. 600/534 |
| 5,348,008 | A | * | 9/1994 | Bornn et al. ............. 600/301 |
| 5,513,646 | A | * | 5/1996 | Lehrman et al. .......... 600/529 |
| 5,611,349 | A | * | 3/1997 | Halleck et al. ........... 600/534 |
| 5,853,005 | A | | 12/1998 | Scanlon |
| 5,938,626 | A | * | 8/1999 | Sugerman .................. 601/6 |
| 6,047,203 | A | * | 4/2000 | Sackner et al. ........... 600/388 |
| 6,210,345 | B1 | * | 4/2001 | Van Brunt ................ 600/529 |
| 6,551,252 | B2 | * | 4/2003 | Sackner et al. ........... 600/536 |
| 6,783,498 | B2 | * | 8/2004 | Sackner et al. ........... 600/481 |
| 7,173,437 | B2 | * | 2/2007 | Hervieux et al. .......... 324/663 |
| 7,267,652 | B2 | * | 9/2007 | Coyle et al. ............. 600/538 |
| 2004/0143194 | A1 | * | 7/2004 | Kihara et al. ............ 600/534 |

FOREIGN PATENT DOCUMENTS

EP         0 919 184 A1     6/1999

* cited by examiner

150 WEARER SIDE

160 NON WEARER SIDE

170 NON WEARER SIDE

PULMONARY EVALUATION DEVICE

FIELD OF THE INVENTION

The present invention relates to pulmonary evaluation devices.

BACKGROUND TO THE INVENTION

The main function of the lungs is to provide continuous gas exchange between inspired air and the blood in the pulmonary circulation, supplying oxygen and removing carbon dioxide, which is then cleared from the lungs by subsequent expiration. Survival is dependent upon this process being reliable, sustained and efficient, even when challenged by disease or an unfavourable environment.

Lung function tests evaluate how much air lungs can hold, how quickly air moves in and out of the lungs, and how well lungs add oxygen to and remove carbon dioxide from the blood. Such tests can help diagnose lung diseases and measure the severity of lung problems that prevent normal breathing.

Lung function tests are done to:

Help determine the cause of breathing problems;

Measure the amount of lung function in a person who has a lung disease and monitor the effectiveness of treatment;

Identify people at high risk of developing lung disease (especially smokers);

Evaluate a person's ability to breathe before surgery;

Monitor the lung function of a person who is regularly exposed to substances that can damage the lungs.

Several different types of tests can provide information about lung function. Such tests include spirometry, gas dilution tests, body plethysmography, carbon monoxide diffusing capacity and arterial blood gases.

Spirometry measures the volume of air inspired or expired as a function of time and is the standard method for measuring most relative lung volumes; however, it is incapable of providing information about absolute volumes of air in the lung. Thus a different approach is required to measure residual volume, functional residual capacity and total lung capacity.

Two methodologies most commonly used for determination of absolute lung volume are gas dilution and body plethysmography.

Gas dilution tests measure the amount of air that remains in the lungs after the subject has exhaled as completely as possible (residual volume). Body plethysmography measures the total amount of air that lungs can hold.

During body plethysmography, the subject sits in an air-tight box (body plethysmograph, or 'body box') of known volume and breathes through a mouthpiece connected to a shutter. The pressure is monitored in two places, in the box and at the subject's airways, the latter via a side-port of the mouthpiece. At end-expiration the airways are momentarily occluded by the shutter, and the subject makes an inspiratory effort against the occlusion. The increase in their chest volume slightly reduces the box volume whilst slightly increasing the pressure in the box.

Monitoring changes in pressure in the box and applying a series of well documented derivation techniques, body plethysmography allows a number of pulmonary measurements to be obtained such as for example thoracic gas volume and airways resistance.

Drawbacks associated with body plethysmography:

Mental confusion, muscular incoordination, body casts or other conditions that prevent the subject from entering the plethysmograph cabinet or adequately performing the required manoevours (i.e. panting against a closed shutter);

Claustrophobia may be aggravated by entering the plethysmography cabinet;

Presence of devices or other conditions such as continuous I.V infusions with pumps or other equipment that will not fit into the plethysmograph that should not be discontinued, or that might interfere with pressure changes (eg. chest tube or ruptured eardrums);

Continuous oxygen therapy that should not be temporarily discontinued;

Over estimation of thoracic gas volumes in subjects with severe obstruction or induced bronchospasm unless a slow 'panting' speed is maintained;

Erroneous measurement of thoracic gas volume, airways resistance, or specific airways conductance due to improper panting technique. Excessive pressure fluctuations or signal drift during panting may invalidate thoracic gas volume, airways resistance or specific airways conductance;

Whole-body plethysmographs are expensive and usually found in pulmonary function laboratories, cardiopulmonary laboratories, clinics and specialist pulmonary offices.

An object of the present invention is to provide a cost effective and easy to use, pulmonary evaluation device which does away with the requirement of the patient having to be placed in an air-tight box so that, for example, it can be used at the General Practice (GP) level.

A further object of the invention is to provide a pulmonary evaluation device that can be used by a variety of subjects or users. Such subjects including neonatal, paediatric, geriatric, disabled, the mentally frail and animals.

SUMMARY OF THE INVENTION

According to the broadest independent aspect of the invention there is provided a pulmonary evaluation device comprising:

sensor means adapted to sense fluctuations in a user's lung operation; and feedback means, driven by said sensor means, for determining successive values representative of the user's lung fluctuations and adapted to translate said values into appropriate lung-evaluating information;

characterised by the feature that the sensor means comprises or forms part of an item suitable to be worn by or carried adjacent the user.

This combination of features is advantageous because it eliminates the requirement of using an enclosure to obtain results useful in pulmonary evaluation. Due to its versatility it is also particularly advantageous because a variety of subjects (even animals) may benefit from its use.

It is also advantageous because it may be used to obtain results without requiring the patient to be sitting in the enclosure. He/she may for example be sitting on his/her hospital bed.

One of the advantages of this particular configuration is in allowing the user to freely move around and change position rather than being static and seated during use. This may for example be particularly useful in assessing pulmonary function during motion or even exercise. Pulmonary evaluation may be obtained for athletes, greyhounds and horses. This enables a range of measurements to be taken during both inactive and active periods to obtain a more detailed and precise profile of the user's lung operation.

According to a subsidiary aspect of the present invention there is provided a device, wherein the item engages the user's body, when in use, so as to follow body movements caused by the user's lung operation.

One of the advantages of such an arrangement is that having the item in engagement allows more accurate measurements to be obtained.

A further advantage of such an arrangement is that compliance measurements may be obtained for specific body parts for example, differentiation between the individual's lungs and/or differentiation between the lungs and the abdomen.

According to a subsidiary, aspect of the present invention there is provided a device, wherein said sensing means incorporate:

an inner wall and an outer wall forming a chamber therebetween; and at least one sensor adapted to sense pressure values within said chamber.

Such a configuration is advantageous in that pressure readings are obtained without the need for an enclosure. The result of this device will therefore generate results which can be readily interpreted by the skilled man in the art without requiring extensive training from his/her knowledge of prior art pulmonary evaluation devices.

In a further subsidiary aspect of the present invention there is provided a device wherein the inner wall is substantially resilient and the outer wall is substantially rigid in relation to the inner wall, whereby the inner wall may follow, in use, the movement caused by the user's lung operation whilst the outer wall remains substantially rigid.

One of the advantages of such an arrangement is that, in use, the user's movements are not restricted.

A further advantage of this particular configuration is that the user may wear the device over its clothing.

Another advantage is that multiple users of differing shapes and sizes may use the device without adjustment.

In a further subsidiary aspect of the present invention, said item is a vehicle seatbelt.

This configuration is particularly advantageous because the tension and/or lack of tension apparent on the seat belt whilst breathing may provide an alternative useable measure of the user's lung operation.

In a further subsidiary aspect of the present invention there is provided a device, wherein said sensor means is a camera whereby said camera captures successive images of the user's lung fluctuations.

Thus a completely non-contact evaluation can be obtained beneficial to, for example, burns victims and/or patients requiring an environment free from contaminants.

DETAILED DESCRIPTION OF THE DRAWINGS

Figure 1A:
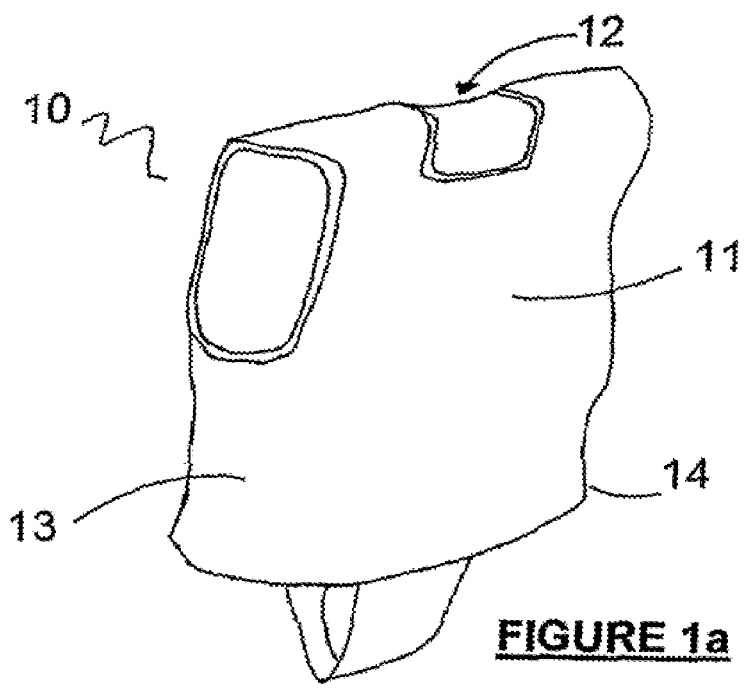
FIGS. 1a and 1b show a front view of a pulmonary evaluation device in accordance with a first embodiment of the invention.
Figure 1B:
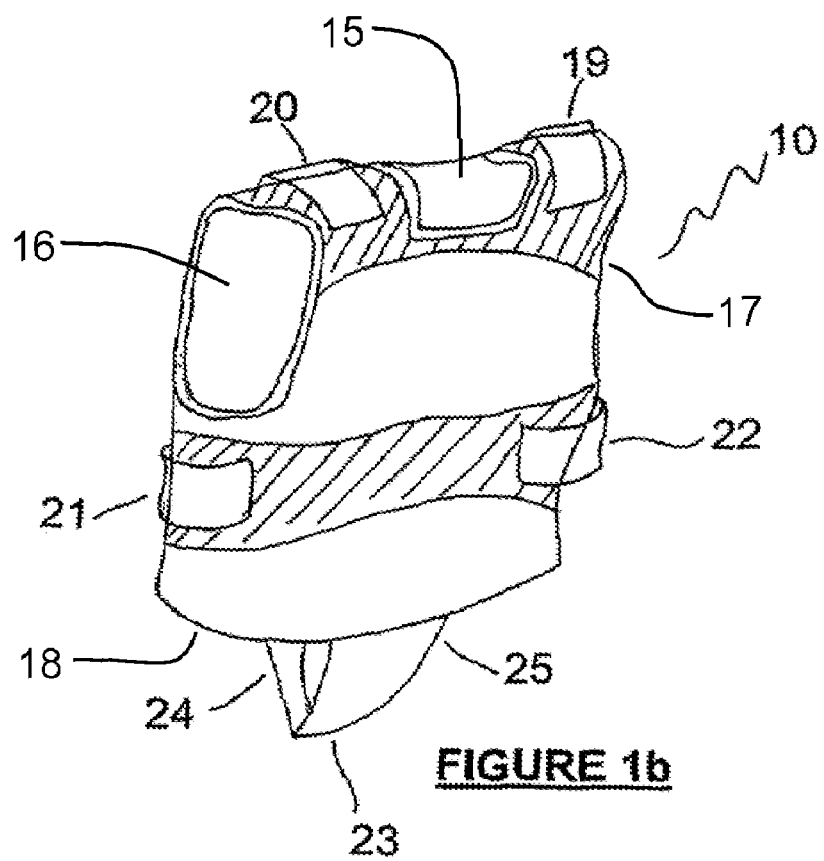

FIG. 1a presents a pulmonary evaluation device 10 in the form of an over-the-head item or garment 10 having a front panel 11, rear panel 12 and side panels 13, 14. FIG. 1b shows device 10 comprising head aperture 15, arm or upper torso apertures 16, 17, lower torso aperture 18, upper adjustment means 19, 20 and/or side adjustment means 21, 22 and securing means 23 for securing between the legs of a patient forming leg apertures 24, 25 in use.

The various apertures are so sized and shaped by the person skilled in the art to allow relatively unrestrained movement of the various body members.

The lower torso aperture 18 is so sized and shaped to allow entry of the user's upper body when donning the garment 10.

Adjustment means 19, 20, 21, 22 are provided between the upper front panel 11, the upper rear panel 12, and side panels 13, 14 such that the user can adjust the garment 10 in use to become more or less form fitting. These may be selected by the skilled man from known alternatives such as VELCRO®.

Securing means 23 is fixably attached at a first end to either the lower front panel 11 or the lower rear panel 12 and releasably connected to the opposing panel 12, 11 at a second end. Once secured the lower torso aperture 18 and securing means 23 provide leg apertures 24, 25 allowing unrestricted movement of the user's legs.

The material forming the garment 10 may be lightweight, supple and form fitting.

When donned the garment 10 covers the anterior chest wall and at least the upper abdomen. The adjustment means 19, 20, 21, 22 provide adjustment ensuring that the necessary region is in sufficient contact with the garment 10.

Figure 2A:
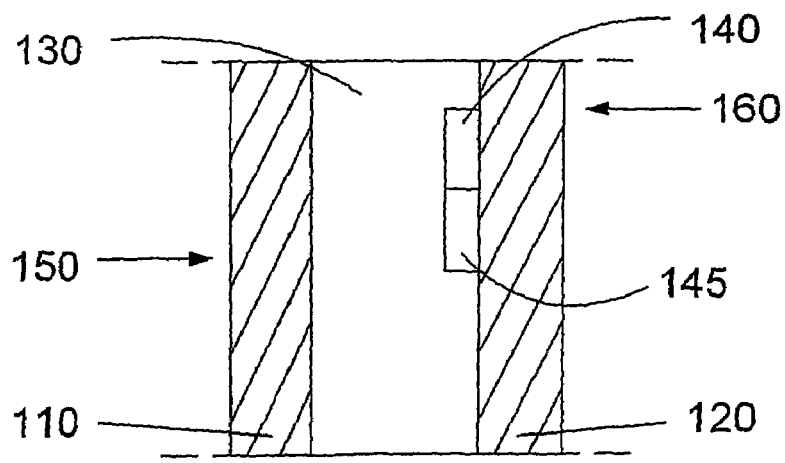
FIGS. 2a-c show cross-sectional views of a pulmonary evaluation device at rest, during inspiration and during expiration.
Figure 2B:
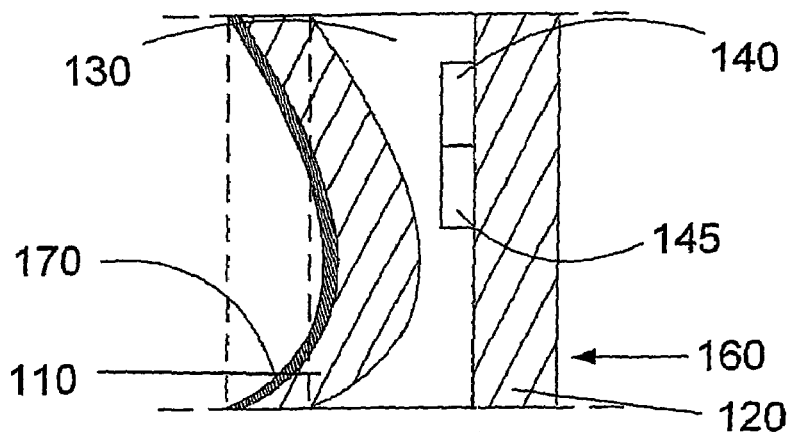
Figure 2C:
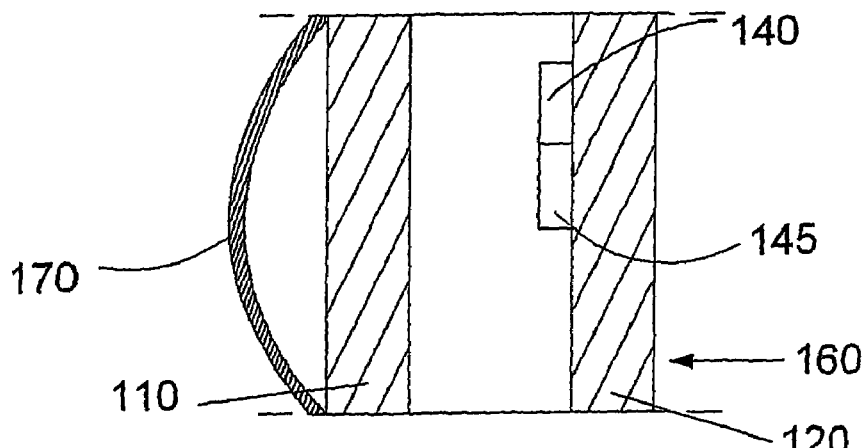

FIGS. 2a-c presents the internal configuration of the garment 10 comprising an inner wall 110 substantially in contact with the user and an outer wall 120 connected to the inner wall 110 and forming a chamber 130 between the inner wall 110 and outer wall 120. Sensor means 140 are located between the two walls 110, 120. Feedback means 145 are connected to the sensor means 140 to capture and evaluate successive readings. Such feedback means may include for example, a microprocessor, a computer or a data logger.

In use, the wearer inserts their head, arms and upper torso through the lower torso aperture 18 until the head exits the head aperture 15 and the arms exit the arm apertures 16, 17. The user and/or assistant adjusts the garment 10 ensuring that the anterior chest wall and the upper abdomen is enclosed by the garment 10. The securing means 23 is secured so as not to restrict the movement of the user's legs or movement of the garment 10 perpendicular to the user's spine whilst restricting the movement of the garment 10 parallel to the user's spine.

The movement of the wearer's chest wall during breathing is followed by the garment 10.

FIGS. 2a to 2c relate the use of the garment 10 to the breathing cycle:

FIG. 2a shows the device 10 at rest;

FIG. 2b shows the device 10 during inspiration wherein the inner wall 110 of the garment 10 follows the movement of the chest. Whereas the outer wall 120 does not. The fixed volume of gas between the inner and outer wall is compressed as the inner wall 110 is pushed towards the outer wall 120 due to the expansion of the lung(s). The volume of gas within the garment 10 does not change whilst the wearer is breathing unlike the pressure of the gas. The sensor means 140 is positioned to note the pressure changes.

FIG. 2c shows the device 10 during expiration, as the lung and chest volume decrease, the inner wall 110 relaxes whilst still following the movement of the chest and the pressure exerted on the gas by the inner wall 110 decreases.

During exercise or rigorous movement the securing means 23 ensures that the garment 10 is correctly located during use.

Figure 3A:
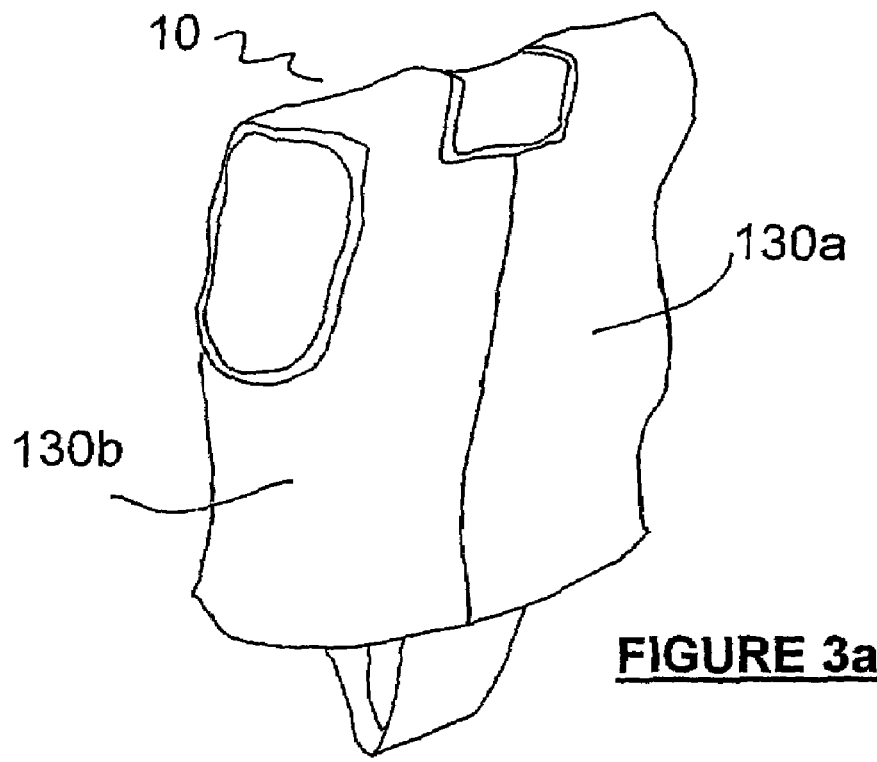
FIGS. 3a-b show front views of a pulmonary evaluation device in accordance with a first embodiment of the invention having an array of chambers.
Figure 3B:
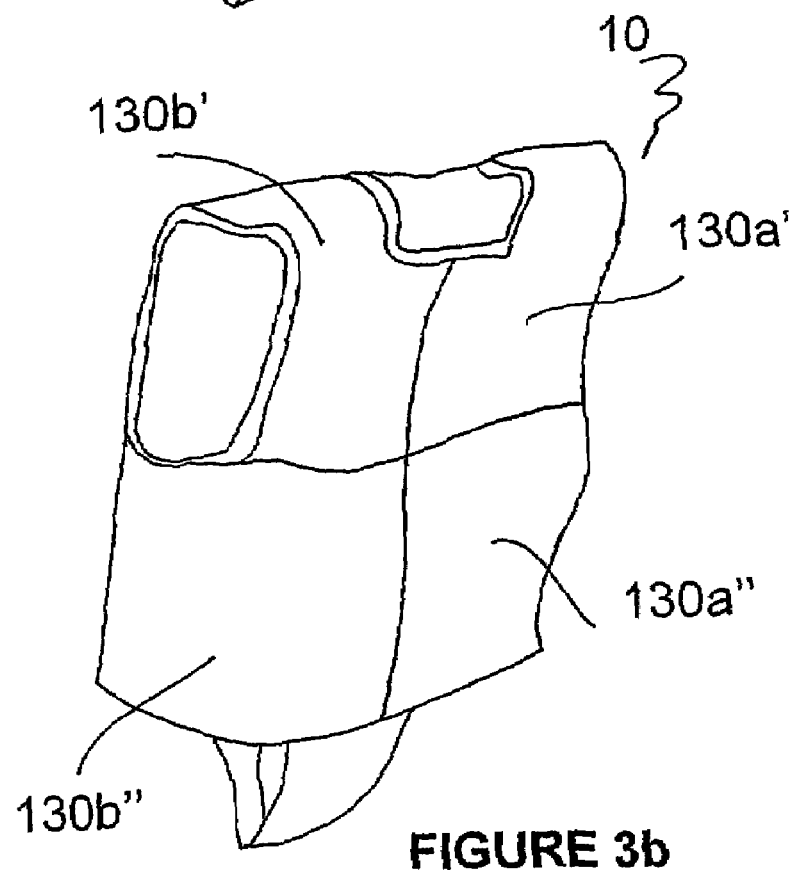

FIGS. 3*a*-*b* present possible configurations of the garment 10 comprising an array of chambers 103*a*, 130*b*, 130*a*', 130*a*", 130*b*', 130*b*".

FIG. 3*a* shows the device 10 having two chambers 130*a*, 130*b* which may be used to differentiate between each lung. Alternatively the front panel 11 may comprise an upper and a lower chamber which may be used to differentiate measurements between the upper rib regions and the lower rib regions.

FIG. 3*b* shows the device 10 having four chambers 130*a*', 130*a*", 130*b*', 130*b*" which may be used to differentiate measurements between the upper and lower rib region of each lung.

The rear panel 12 may have a similar array of chambers as just described.

The number and location of the array of chambers 130*a*, 130*b*, 130*a*', 130*a*", 130*b*', 130*b*" permit localised measurements to be obtained.

In a second embodiment the pulmonary evaluation device may take the form of a vehicle seat belt having a pulmonary contact region enclosing the torso and sensor means within the pulmonary contact region capable of measuring tension within the contact region, all being connected to a microprocessor which stores and evaluates the obtained results.

Alternatively the sensor means may comprise a dual wall structure having a sensor therebetween as previously described. Such a vehicle seat belt variant would enable heart compliance measurements to be obtained if the contact region was located over the heart.

In a third embodiment, the pulmonary evaluation device utilises a camera monitoring lung fluctuation/displacement. As the user breathes a number of images of the user's chest wall profile can be captured and then processed to determine displacement during breathing.

The invention claimed is:

1. A pulmonary volume evaluation device comprising:
   an item worn over the user's body for following body movements caused by the user's lung operation;
   said item comprising:
   a front panel corresponding to the user's front;
   a rear panel corresponding to the user's back;
   an upper aperture sized and shaped to allow the user's head to be outside the item when worn;
   a lower aperture sized and shaped to allow the user's legs to be outside the item when worn;
   said front panel extending from said upper aperture to said lower aperture and being sized and shaped to substantially entirely cover the anterior chest wall and at least the upper abdomen;
   a sensor for sensing fluctuations in a user's lung operation; and
   feedback means, driven by said sensor, for determining successive values representative of the user's lung fluctuations and for translating said values into appropriate lung-evaluating information;
   wherein said item has at least one chamber located in both said front and rear panels formed between an inner wall and an outer wall, said at least one chamber having a substantially enclosed volume of gas disposed therein, said at least one chamber being sized and shaped so as to substantially entirely cover the chest wall and at least the upper abdomen of the user's body, said inner wall being spaced from said outer wall throughout the entire lung region and being substantially flexible to remain in contact with the entire lung region in order to follow, in use, the displacement of the entire lung region; and said outer wall is substantially rigid in order to remain in position during the displacement of the lung region; whereby said inner wall and said outer wall combine to compress said volume of gas as said flexible inner wall is pushed towards said rigid outer wall during inspiration as the lungs expand and to decompress said volume of gas as said flexible inner wall relaxes during expiration as the lungs contract; and said sensor senses changes in pressure within said chamber throughout inspiration and expiration.

2. A device according to claim 1, comprising a seal for sealing said at least one chamber; whereby the volume of gas contained by said at least one chamber remains constant and as the body displaces during respiration, a measurable change in internal chamber pressure occurs as the chamber's wall displaces.

3. A device according to claim 1, incorporating an array of chambers locating a chamber over a separate region of the user's lung.

4. A device according to claim 1, wherein said at least one chamber comprises two chambers each of which correspond to a lung.

5. A device according to claim 1, wherein said at least one chamber comprises four chambers each of which correspond to one of an upper rib region and a lower rib region of a lung.

6. A device according to claim 1, wherein said feedback means comprises at least one of a microprocessor, a computer, and a data logger.

7. A device according to claim 1, wherein said item incorporates at least one adjustable fixing.

8. A device for determining pulmonary volume of a user, the device comprising:
   an item;
   said item comprising:
   a front panel corresponding to the user's front;
   a rear panel corresponding to the user's back;
   an upper aperture sized and shaped to allow the user's head to be outside the item when worn;
   a lower aperture sized and shaped to allow the user's legs to be outside the item when worn;
   said front panel extending from said upper aperture to said lower aperture and being sized and shaped to substantially entirely cover the anterior chest wall and at least the upper abdomen;
   said item comprising an inner wall and an outer wall, the inner wall and the outer wall bounding at least one chamber therebetween located in both said front and rear panel, a substantially enclosed volume of gas being disposed within the at least one chamber, the item being configured to be worn over the body of the user and the chamber being sized and shaped so as to substantially entirely cover the chest wall and at least the upper abdomen of the user when the item is worn over the body of the user, said inner wall being spaced from said outer wall throughout the entire lung region and being substantially flexible to remain in contact with the entire lung region in order to follow in use the displacement of the entire lung region, and said outer wall being substantially rigid in order to remain in position during the displacement of the lung region; whereby the inner wall and the outer wall are configured to compress the volume of gas as the inner wall is pushed towards the outer wall as a result of the lungs of the user expanding during inspiration and to decompress the volume of gas as the inner wall relaxes as a result of the lungs of the user contracting during expiration;

a sensor being configured to sense changing pressure values of the volume of gas within the chamber; and means for capturing and evaluating successive pressure values from the sensor to determine values representative of lung fluctuations of the user and for translating said values into appropriate lung-evaluating information.

9. A device according to claim 8, wherein the means for capturing and evaluating comprises at least one of: a microprocessor, a computer, and a data logger.

10. A device according to claim 8, further comprising a seal that selectively seals the at least one chamber.

11. A device according to claim 8, wherein the at least one chamber comprises an array of chambers configured so that each chamber is positioned over a separate region of the lung when the item is worn over the body of the user.

12. A device according to claim 8, wherein the at least one chamber comprises two chambers configured so that each chamber is positioned over a separate lung when the item is worn over the body of the user.

13. A device according to claim 8, wherein the at least one chamber comprises four chambers configured so that two of the four chambers are respectively positioned over an upper rib region and a lower rib region of a lung, and the other two of the four chambers are respectively positioned over an upper rib region and a lower rib region of the other lung when the item is worn over the body of the user.

14. A device according to claim 8, wherein said item incorporates at least one adjustable fixing.

* * * * *